US012758749B2

(12) United States Patent
Okamoto et al.

(10) Patent No.: US 12,758,749 B2
(45) Date of Patent: Oct. 13, 2026

(54) BALLOON FOR CATHETER

(71) Applicant: GOODMAN CO., LTD., Nagoya (JP)

(72) Inventors: Mitsumasa Okamoto, Seto (JP); Yuta Nakamura, Seto (JP); Shuhei Yamamoto, Seto (JP); Shoma Kondo, Seto (JP); Shizuya Yoshinaga, Seto (JP); Takashi Kunisada, Seto (JP)

(73) Assignee: GOODMAN CO., LTD., Nagoya (JP)

( * ) Notice: Subject to any disclaimer, the term of this patent is extended or adjusted under 35 U.S.C. 154(b) by 117 days.

(21) Appl. No.: 18/393,429

(22) Filed: Dec. 21, 2023

(65) Prior Publication Data

US 2024/0123198 A1 Apr. 18, 2024

Related U.S. Application Data

(63) Continuation of application No. PCT/JP2022/021097, filed on May 23, 2022.

(30) Foreign Application Priority Data

Jun. 22, 2021 (JP) ................................ 2021-103068

(51) Int. Cl.
*A61M 25/10* (2013.01)
*A61M 25/00* (2006.01)

(52) U.S. Cl.
CPC .... *A61M 25/1002* (2013.01); *A61M 25/0043* (2013.01); *A61M 2025/1004* (2013.01); (Continued)

(58) Field of Classification Search
CPC .. A61M 2025/1004; A61M 2025/1086; A61B 17/320725
See application file for complete search history.

(56) References Cited

U.S. PATENT DOCUMENTS 5,196,024 A 3/1993 Barath
5,320,634 A 6/1994 Vigil et al.
(Continued)

FOREIGN PATENT DOCUMENTS

CN 108601929 A 9/2018
CN 112203713 A 1/2021
(Continued)

OTHER PUBLICATIONS

Jul. 31, 2024—(AU) Examination Report No. 1—App 2022298081.
(Continued)

*Primary Examiner* — Brigid K Byrd
(74) *Attorney, Agent, or Firm* — Banner & Witcoff, Ltd.

(57) ABSTRACT

A balloon has an inflatable portion that forms a tube shape extending in an extending direction in an inflated state, a distal end connecting portion provided to an end portion of the inflatable portion on one side thereof, and a proximal end connecting portion provided to an end portion of the inflatable portion on the other side thereof. At least the inflatable portion includes a plurality of first portions that forms wings in the deflated state and a plurality of second portions that is adjacent to the plurality of first portions in a circumferential direction centered on the center axis. In the process of changing shape from the inflated state to the deflated state, the plurality of second portions moves towards the center axis in advance of the plurality of first portions and thereby forms, in the inflatable portion, indentations recessed toward the center axis.

18 Claims, 25 Drawing Sheets

(52) U.S. Cl.
CPC ............... *A61M 2025/1059* (2013.01); *A61M 2025/1086* (2013.01)

(56) References Cited

U.S. PATENT DOCUMENTS

| | | | | |
|---|---|---|---|---|
| 5,458,572 | A | 10/1995 | Campbell et al. | |
| 5,616,149 | A * | 4/1997 | Barath ........... | A61B 17/320725 604/103.08 |
| 5,718,684 | A | 2/1998 | Gupta | |
| 10,729,892 | B2 | 8/2020 | Yamazaki | |
| 12,042,613 | B2 | 7/2024 | Okamoto et al. | |
| 2003/0153870 | A1 * | 8/2003 | Meyer ................. | A61M 25/104 604/96.01 |
| 2004/0133223 | A1 | 7/2004 | Weber | |
| 2006/0015134 | A1 | 1/2006 | Trinidad | |
| 2006/0149308 | A1 * | 7/2006 | Melsheimer ... | A61B 17/320725 606/192 |
| 2010/0234874 | A1 | 9/2010 | Burton | |
| 2011/0160756 | A1 | 6/2011 | Aggerholm et al. | |
| 2018/0043140 | A1 * | 2/2018 | Iwano ................. | A61M 25/104 |
| 2018/0280666 | A1 | 10/2018 | Yamazaki | |
| 2019/0091452 | A1 | 3/2019 | Fujisawa et al. | |
| 2021/0077790 | A1 | 3/2021 | Iwano et al. | |
| 2021/0113820 | A1 | 4/2021 | Okamoto et al. | |
| 2022/0184353 | A1 | 6/2022 | Koga et al. | |
| 2022/0323728 | A1 * | 10/2022 | Koga ................ | A61M 25/1029 |

FOREIGN PATENT DOCUMENTS

| | | | |
|---|---|---|---|
| JP | S62-114565 | A | 5/1987 |
| JP | H05-293176 | A | 11/1993 |
| JP | H10-506296 | A | 6/1998 |
| JP | 2006-512952 | A | 4/2006 |
| JP | 2008-506454 | A | 3/2008 |
| JP | 2018-171318 | A | 11/2018 |
| WO | 1996001133 | A1 | 1/1996 |
| WO | 2004060460 | A2 | 7/2004 |
| WO | 2006016938 | A1 | 2/2006 |
| WO | 2020-195697 | A1 | 10/2020 |
| WO | 2021049282 | A1 | 3/2021 |

OTHER PUBLICATIONS

Jul. 26, 2023—International Search Report—Intl App PCT/JP2022/021097.
Jul. 16, 2025—(CA) Action—App 3,221,680.
Sep. 17, 2024—(JP) Notice of Reasons for Refusal—App 2023-529709.
May 19, 2025—(EP) Extended Search Report—App 22828111.9.
Dec. 14, 2023—(WO) IPRP—App PCT/JP2022/021097.
Nov. 23, 2025—(KR) Office Action—App 10-2024-7000184.
Nov. 26, 2025—(CN) First Office Action—App 202280021598.5.
Feb. 11, 2026—(IN) First Examination Report—App 202417003637.
Feb. 13, 2026—(CN) Rejection Decision—App 202280021598.5.
Aug. 18, 2026—(CA) Office Action—App 3,221,680.

* cited by examiner

BALLOON FOR CATHETER

REFERENCE TO RELATED APPLICATIONS

This application is a Continuation Application of International Application No. PCT/JP2022/021097, filed May 23, 2022, which claims priority from Japanese Patent Application No. 2021-103068, filed on Jun. 22, 2021. This disclosure of the foregoing application is hereby incorporated by reference in its entirety.

BACKGROUND ART

To improve the passability of a balloon catheter through a blood vessel, it is preferable that a diameter of a balloon in a deflated state be as small as possible. A balloon catheter is known that is held by a holder in a state in which a diameter thereof is minimized by winding a folded balloon thin film around a support member. At a time of use, the balloon catheter is used after being removed from the holder.

SUMMARY

A balloon preferably has a small diameter even after being inflated inside a blood vessel at a time of use and subsequently being deflated. However, in the above balloon catheter, the diameter is made smaller as a result of the state of the balloon thin film wound around a support portion being maintained by the holder. Thus, there is a possibility that the diameter cannot be made smaller in a state in which the balloon thin film is removed from the holder. Thus, for example, when the balloon thin film is removed from the holder and is inflated at the time of use, and the balloon thin film is subsequently deflated after use and removed from the body, there is a possibility that the diameter of the deflated balloon thin film may increase and the removal may be difficult.

An object of the present disclosure is to provide a balloon for a catheter capable of minimizing a diameter thereof, even when deflated after being inflated.

A catheter according to a first aspect of the present disclosure is capable of being in an inflated state and a deflated state in accordance with changes in internal pressure. The balloon for a catheter includes an inflatable portion, a distal end connecting portion, and a proximal end connecting portion. The inflatable portion is configured to, in a process of changing shape from the deflated state to the inflated state, inflate by moving to the outside in a radial direction centered on a center axis extending in a predetermined extending direction, and to form a tube shape extending in the extending direction in the inflated state. The distal end connecting portion is a portion extending from a distal end portion of the inflatable portion. The distal end portion is an end portion on one side in the extending direction. In the inflated state, a diameter of the distal end connecting portion at one end portion is larger than a diameter at the other end portion. The one end portion is an end portion connected to the inflatable portion. The other end portion is an end portion on an opposite side to the one end portion. The proximal end connecting portion is a portion extending from a proximal end portion of the inflatable portion. The proximal end portion is an end portion on the other side in the extending direction. In the inflated state, a diameter of the proximal end connecting portion at one end portion is larger than a diameter of the other end portion. The one end portion is an end portion connected to the inflatable portion. The other end portion is an end portion on an opposite side to the one end portion. At least the inflatable portion includes a plurality of first portions and a plurality of second portions. The plurality of first portions forms wings in the deflated state. The plurality of second portions is adjacent to the plurality of first portions in a circumferential direction centered on the center axis in the inflated state. The plurality of second portions causes formation of indentations recessed toward the center axis, by moving toward the center axis in advance of the plurality of first portions, in the process of changing shape from the inflated state to the deflated state.

In the balloon for the catheter according to the first aspect, when changing shape from the inflated state to the deflated state, the plurality of second portions moves toward the center axis in advance of the plurality of first portions, and the plurality of wings is formed by each of the plurality of first portions. In this case, even when the balloon for the catheter repeatedly changes shape between the inflated state and the deflated state, the balloon for the catheter is always folded into a stable shape. Thus, the diameter of the balloon for the catheter can be reduced in the deflated state.

A balloon for a catheter according to a second aspect of the present disclosure is capable of being in an inflated state and a deflated state in accordance with changes in internal pressure. The balloon for a catheter includes an inflatable portion, a distal end connecting portion, and a proximal end connecting portion. The inflatable portion is configured to, in a process of changing shape from the deflated state to the inflated state, inflate by moving to the outside in a radial direction centered on a center axis extending in a predetermined extending direction, and to form a tube shape extending in the extending direction in the inflated state. The proximal end connecting portion is a portion extending from a proximal end portion of the inflatable portion. The proximal end portion is an end portion on the other side in the extending direction. In the inflated state, a diameter of the proximal end connecting portion at one end portion is larger than a diameter of the other end portion. The one end portion is an end portion connected to the inflatable portion. The other end portion is an end portion on an opposite side to the one end portion. At least the inflatable portion includes a plurality of first portions and a plurality of second portions. The plurality of first portions forms wings in the deflated state. The plurality of second portions is adjacent to the plurality of first portions in a circumferential direction centered on the center axis in the inflated state. In the inflated state, a distance, in the radial direction, from the center axis to each of the plurality of second portions is shorter than a distance, in the radial direction, from the center axis to each of the plurality of first portions.

In the balloon for the catheter according to the second aspect, when changing shape from the inflated state to the deflated state, the plurality of second portions having the shorter distance to the center axis in the inflated state move toward the center axis first, and the wings are formed by each of the plurality of first portions. In this case, even when the balloon for the catheter repeatedly changes shape between the inflated state and the deflated state, the balloon for the catheter is always folded into a stable shape. Thus, the diameter of the balloon for the catheter can be reduced in the deflated state.

BRIEF DESCRIPTION OF DRAWINGS

Embodiments will be described below in detail with reference to the accompanying drawings in which.

DESCRIPTION

Embodiments of a balloon catheter 1 (1A to 1E) according to the present disclosure will be described with reference to the accompanying drawings. The referenced drawings are used to describe technical features that can be employed in the present disclosure. The described configurations and the like of the device are not intended to be limited thereto, and are merely examples for explanation purposes. The balloon catheter 1 can dilate a stenotic lesion formed in a blood vessel. Furthermore, the balloon catheter 1 can cause a second portion 5A to be described later to act on the lesion to crush or incise the lesion.

Balloon Catheter 1A

Figure 1:
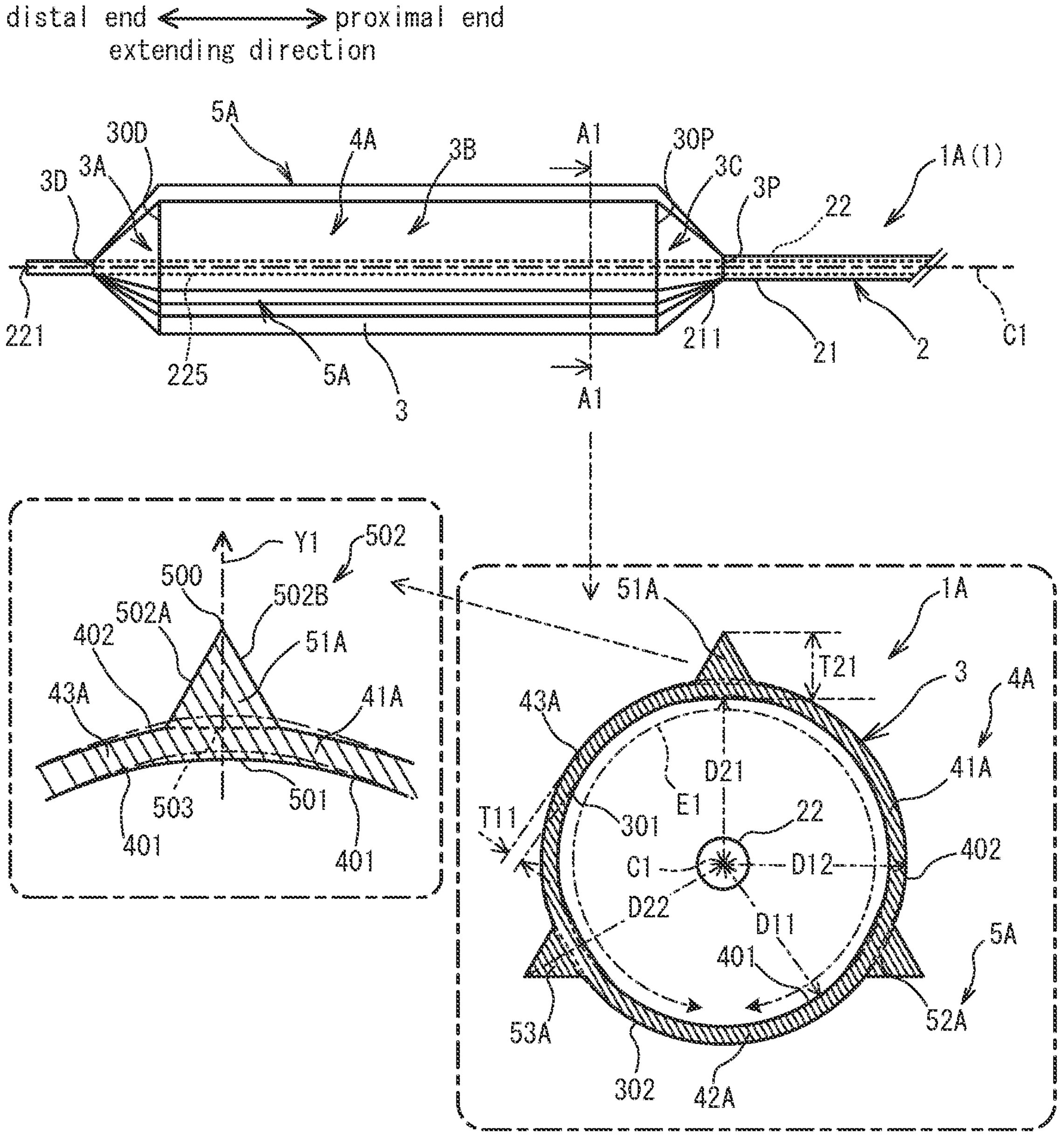
FIG. 1 includes views showing a balloon catheter when a balloon is in an inflated state.

The balloon catheter 1A will be described with reference to FIG. 1. The balloon catheter 1A has a catheter shaft 2 and a balloon 3.

Catheter Shaft 2

The balloon 3 is connected to an end portion on one side of the tube-shaped catheter shaft 2. The balloon catheter 1A is used in a state in which a hub, not shown in the drawings, is connected to an end portion on the other side of the catheter shaft 2. The hub can supply compressed fluid to the balloon 3 via the catheter shaft 2.

The one side from among both ends of the catheter shaft 2 will be referred to as a distal end side. The other side from among both ends of the catheter shaft 2 will be referred to as a proximal end side. A direction extending along the catheter shaft 2 will be referred to as to as an extending direction. An axis passing through a center of the catheter shaft 2 and extending in the extending direction will be referred to as a center axis C1. In a cross section cut on a plane perpendicular to the center axis C1 (hereinafter simply referred to as a cross section), a side closer to the center axis C1 in a radial direction centered on the center axis C1 will be referred to as an inner side, and a side further away from the center axis C1 will be referred to as an outer side.

The catheter shaft 2 has an outer tube 21 and an inner tube 22. The outer tube 21 and the inner tube 22 are both flexible. An inside diameter of the outer tube 21 is larger than an outside diameter of the inner tube 22. Apart from a predetermined portion on the distal end side, the inner tube 22 is disposed inside a lumen of the outer tube 21. The predetermined portion on the distal end side of the inner tube 22 protrudes toward the distal end side from an end (hereinafter referred to as a distal end 211) on the distal end side of the outer tube 21. An end on the distal end side of the inner tube 22 (hereinafter referred to as a distal end 221) is disposed farther to the distal end side than the distal end 211 of the outer tube 21. The predetermined portion on the distal end side of the inner tube 22 will be referred to as a protruding section 225. The material of the outer tube 21 and the inner tube 22 is not particularly limited. A polyamide resin may be used as the material of the outer tube 21 and the inner tube 22, for example.

The compressed fluid supplied from the hub passes through a space of the lumen of the outer tube 21 other than a lumen of the inner tube 22. A guide wire that is not shown in the drawings is inserted through the lumen of the inner tube 22.

Balloon 3

The balloon 3 can change shape between a deflated state and an inflated state, as a result of a change in internal pressure according to whether the compressed fluid is supplied from the hub that is not shown in the drawings. FIG. 1 shows the balloon 3 in the inflated state. An end on the distal end side of the balloon 3 (hereinafter referred to as a distal end portion 3D) is connected by thermal welding to the inner tube 22, in the vicinity of the distal end 221 of the protruding section 225. An end on the proximal end side of the balloon 3 (hereinafter referred to as a proximal end portion 3P) is connected by thermal welding to the outer tube 21, in the vicinity of the distal end 211. The balloon 3 covers the protruding section 225 of the inner tube 22 from the outside. The material of the balloon 3 is not particularly limited. A polyamide resin may be used as the material of the balloon 3, for example.

A distal end connecting portion 3A, an inflatable portion 3B, and a proximal end connecting portion 3C are defined in the balloon 3. The distal end connecting portion 3A is a region extending while increasing in diameter from the distal end portion 3D toward the proximal end portion 3P of the balloon 3 in the inflated state. The proximal end connecting portion 3C is a region extending while increasing in diameter from the proximal end portion 3P toward the distal end portion 3D of the balloon 3 in the inflated state. The inflatable portion 3B is a region sandwiched between the distal end connecting portion 3A and the proximal end connecting portion 3C of the balloon 3 in the inflated state, and a diameter thereof is substantially the same along the extending direction. In the inflated state, the inflatable portion 3B has a tubular shape extending in the extending direction. The balloon 3 has an inner surface 301 and an outer surface 302.

An end on the distal end side of the inflatable portion 3B will be referred to as a distal end portion 30D, and an end on the proximal end side of the inflatable portion 3B will be referred to as a proximal end portion 30P. The distal end connecting portion 3A extends to the distal end side toward the distal end portion 3D, from an end connected to the distal end portion 30D of the inflatable portion 3B. A diameter of the cross section of the distal end connecting portion 3A is largest at the end connected to the distal end portion 30D of the inflatable portion 3B, and is smallest at the distal end portion 3D. The proximal end connecting portion 3C extends to the proximal end side toward the proximal end portion 3P, from an end connected to the proximal end portion 30P of the inflatable portion 3B. A diameter of the cross section of the proximal end connecting portion 3C is largest at the end connected to the proximal end portion 30P of the inflatable portion 3B, and is smallest at the proximal end portion 3P.

The distal end connecting portion 3A, the inflatable portion 3B, and the proximal end connecting portion 3C of the balloon 3 respectively include first portions 41A, 42A, and 43A (hereinafter referred to collectively as a first portion 4A), and second portions 51A, 52A, and 53A (hereinafter referred to collectively as second portion 5A). Each of the first portion 4A and the second portion 5A extends in the extending direction between the distal end portion 3D of the distal end connecting portion 3A and the proximal end portion 3P of the proximal end connecting portion 3C. The first portion 4A and the second portion 5A are formed from the same material.

Of a direction extending along the inflatable portion 3B of the balloon 3, the direction perpendicular to the center axis C1 will be referred to as a circumferential direction E1. The first portion 4A and the second portion 5A are respectively arranged in order, in the circumferential direction E1, of the second portion 51A, the first portion 41A, the second portion 52A, the first portion 42A, the second portion 53A, and the first portion 43A. The first portion 4A and the second portion 5A are adjacent to each other in the circumferential direction E1, and are alternately arranged. The second portions 51A, 52A, and 53A are disposed at equal intervals in the circumferential direction E1. Of the inner surface 301 of the balloon 3, portion corresponding to the first portion 4A will be referred to as an inner surface 401, and portion corresponding to the second portion 5A will be referred to as an inner surface 501. Of the outer surface 302 of the balloon 3, portion corresponding to the first portion 4A will be referred to as an outer surface 402, and portion corresponding to the second portion 5A will be referred to as an outer surface 502.

The rigidity of the first portion 4A and of the second portion 5A differs. The rigidity of the second portion 5A is higher than that of the first portion 4A. Note that the difference in the rigidity between the first portion 4A and the second portion 5A need only be obtained from at least one of results from various well-known rigidity tests. As described above, the first portion 4A and the second portion 5A are formed from the same material, and the difference in the rigidity is generated by causing respective thicknesses thereof to be different.

When the balloon 3 is in the inflated state, the inner surface 401 and the outer surface 402 of the first portion 4A curve in a circular arc shape centered on the center axis C1. A distance in the radial direction between the center axis C1 and the inner surface 401 of the first portion 4A is denoted by D11. A distance in the radial direction between the center axis C1 and the outer surface 402 of the first portion 4A is denoted by D12. A thickness of the first portion 4A in the radial direction corresponds to a distance in the radial direction between the inner surface 401 and the outer surface 402, and is denoted by T11. More specifically, a curvature at both of end portions in the circumferential direction E1 of the inner surface 401 and the outer surface 402 is slightly greater than a curvature of portions excluding both end portions (refer to FIG. 2C and FIG. 3A).

The outer surface 502 of the second portion 5A has an apex 500 protruding furthest to the outer side in the radial direction. The outer surface 502 has outer surfaces 502A and 502B corresponding to two side surfaces of a triangular shape in cross section. Of the outer surfaces 502A and 502B, an end portion on an opposite side from the apex 500 is connected to an end portion of the first portion 4A that is adjacent in the circumferential direction E1. Of the outer surfaces 502A and 502B, a plane linking the apex 500 and the end portion on the opposite therefrom will be referred to as a bottom surface 503. A direction extending perpendicularly to the bottom surface 503 and extending from the bottom surface 503 and passing through the apex 500 will be referred to as a protruding direction Y1. In the inflated state, the protruding direction Y1 is oriented to the outside in the radial direction. The inner surface 501 of the second portion 5A is positioned on the inner side of the bottom surface 503 in the radial direction. A distance between the center axis C1 and the inner surface 501 of the second portion 5A is denoted by D21. A distance between the center axis C1 and the apex 500 is denoted by D22. A thickness of the second portion 5A in the radial direction corresponds to a distance in the radial direction between the inner surface 501 and the apex 500 of the second portion 5A and is denoted by T21.

The thickness T21 in the radial direction of the second portion 5A in the inflatable portion 3B is the same in the extending direction. The thickness T21 in the radial direction of the second portion 5A in the distal end connecting portion 3A is largest at the portion connected to the distal end portion 30D of the inflatable portion 3B, and becomes smaller the closer to the distal end portion 3D. The thickness T21 in the radial direction of the second portion 5A in the proximal end connecting portion 3C is largest at the portion connected to the proximal end portion 30P of the inflatable portion 3B, and becomes smaller the closer to the proximal end portion 3P.

In any chosen cross section in the extending direction, the thickness T21 of the second portion 5A is larger than the thickness T11 of the first portion 4A. In the inflated state, the distance D21 between the inner surface 501 of the second portion 5A and the center axis C1 is shorter than the distance D11 between the inner surface 401 of the first portion 4A and the center axis C1. In other words, a distance from the center axis C1 to the second portion 5A in the radial direction is shorter than a distance from the center axis C1 to the first portion 4A in the radial direction. In the inflated state, the distance D22 between the outer surface 502 of the second portion 5A and the center axis C1 is longer than the distance D12 between the outer surface 402 of the first portion 4A and the center axis C1.

Figure 2A:
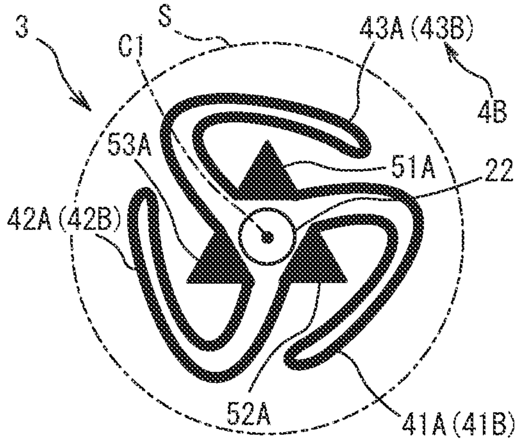
FIG. 2A is views showing the balloon changing shape from a deflated state to the inflated state.
Figure 2B:
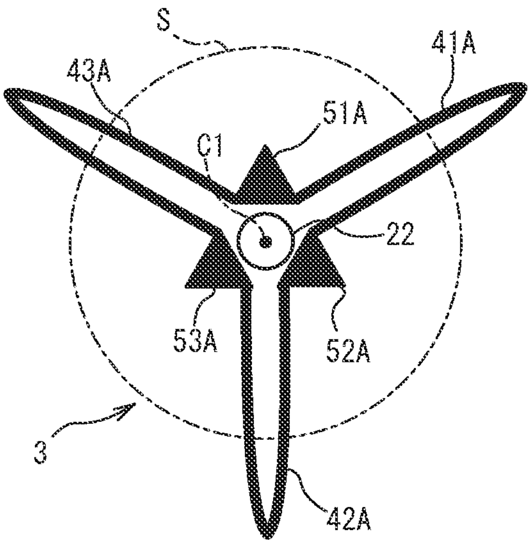
FIG. 2B is views showing the balloon changing shape from a deflated state to the inflated state.
Figure 2C:
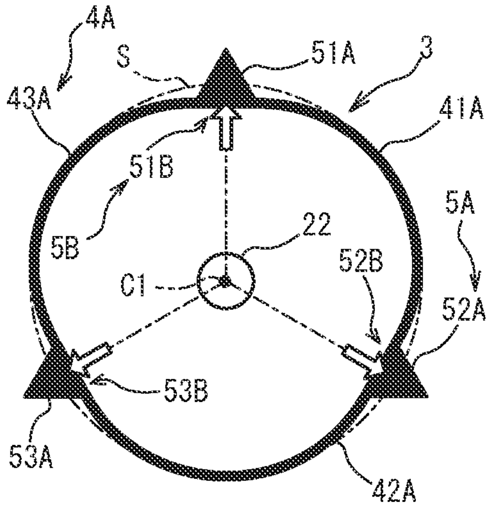
FIG. 2C is views showing the balloon changing shape from a deflated state to the inflated state.
Figure 3A:
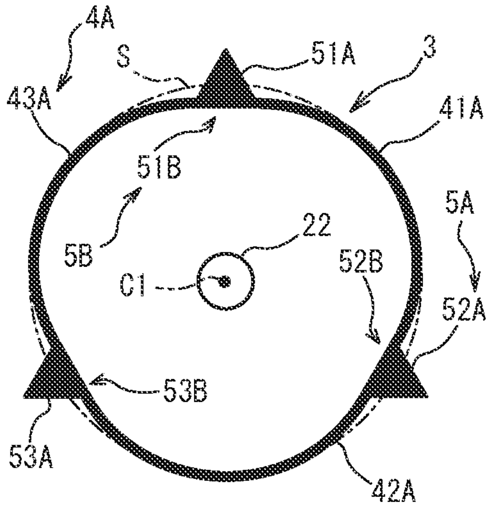
FIG. 3A is views showing the balloon changing shape from the inflated state to the deflated state.
Figure 3B:
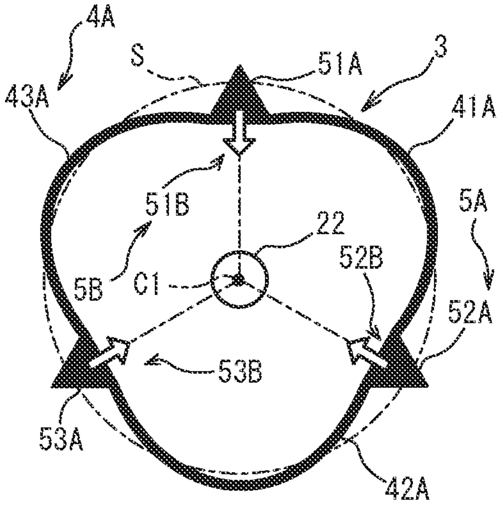
FIG. 3B is views showing the balloon changing shape from the inflated state to the deflated state.

As shown in FIG. 2C, in the cross section of the balloon 3 in the inflated state, a virtual circle S in contact from an outside with the first portions 41A to 43A is defined. In this case, both of end portions in the circumferential direction E1 of each of the first portions 41A to 43A, and portions in closer proximity to the center axis C1 than the bottom surface 503 (refer to FIG. 1) of each of the second portions 51A to 53A are all positioned inside the virtual circle S. Thus, indentations 51B, 52B, and 53B (hereinafter referred to collectively as an indentation 5B), in which the second portions 51A, 52A, and 53A are recessed toward the center axis C1, are formed in the balloon 3. Note that the balloon 3 is caused to remember the shape of the state in which the indentations 51B, 52B, and 53B are formed in the second portions 51A, 52A, and 53A, such that the shape is stabilized.

Note that the method of causing the shape of the first portion 4A to be remembered is not particularly limited. For example, the balloon 3 may be created by blow molding using a die having the same shape as the balloon 3 in the state in which the indentation 5B is formed in the second portion 5A. In this case, it is possible to manufacture the balloon 3 that remembers the shape of the state in which the indentation 5B is formed in the second portion 5A.

As shown in FIG. 2A, the balloon 3 in the deflated state has wings 41B, 42B, and 43B (hereinafter collectively referred to as a wing 4B). The wings 41B, 42B, and 43B are formed by each of the first portions 41A, 42A, and 43A of the balloon 3 being folded and wound onto the second portions 52A, 53A, and 51A, respectively, from the outside. The second portion 5A is covered from the outside by the wing 4B. The wing 4B is also referred to as a flap or a wing.

Deflation/Inflation of Balloon 3

FIG. 2 shows a process of the balloon 3 changing shape from the deflated state to the inflated state. It is assumed that the compressed fluid is supplied from the hub (not shown in the drawings) to the balloon 3 in the deflated state shown in FIG. 2A. In this case, as shown in FIG. 2B. the first portions 41A to 43A of the balloon 3 expand and the wings 41B to 43B (refer to FIG. 2A) are freed. Further, when the compressed fluid is supplied to the balloon 3, each of the second portions 51A to 53A moves to the outside in the radial direction, and moves away from the center axis C1. As a result, as shown in FIG. 2C, the balloon 3 is in the inflated state. Note that in FIG. 2C, in order to make the indentations 51B, 52B, and 53B easy to understand, a recess amount of the indentations 51B, 52B, and 53B is larger than an actual recess amount (the recess amount of the indentations 51B, 52B, and 53B shown in FIG. 1). This also applies to FIG. 3A to be described later.

FIG. 3 shows a process of the balloon 3 changing shape from the inflated state to the deflated state. The compressed fluid is removed from the balloon 3 in the inflated state shown in FIG. 3A. Here, as described above, the balloon 3 is caused to remember the shape of the state in which the indentations 51B, 52B, and 53B are formed in the second portions 51A, 52A, and 53A. Thus, as shown in FIG. 3B, in accordance with the removal of the compressed fluid, the whole of the balloon 3 moves toward the center axis C1 by a predetermined amount, and subsequently, the second portions 51A to 53A move toward the center axis C1 in advance of the first portions 41A to 43A. As a result, the recess amount of the indentations 51B to 53B with respect to the virtual circle S is larger than in the inflated state.

Note that, in the cross section, the thickness T21 of the second portion 5A in the radial direction is larger than the thickness T11 of the first portion 4A in the radial direction, and thus, a speed at which the second portions 51A to 53A move toward the center axis C1 is slow immediately after the start of moving, and thereafter becomes faster. Note that the recess amount of the indentations 51B to 53B is larger at the inflatable portion 3B than at the distal end connecting portion 3A and the proximal end connecting portion 3C. Thus, a maximum diameter of the balloon 3, that is a diameter of the inflatable portion 3B, becomes rapidly smaller.

Figure 3C:
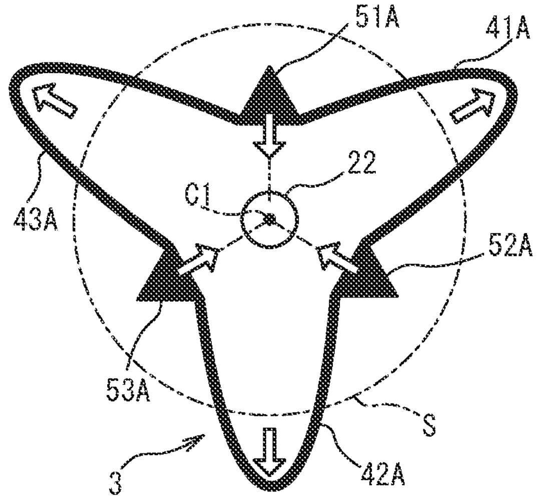
FIG. 3C is views showing the balloon changing shape from the inflated state to the deflated state.
Figure 3D:
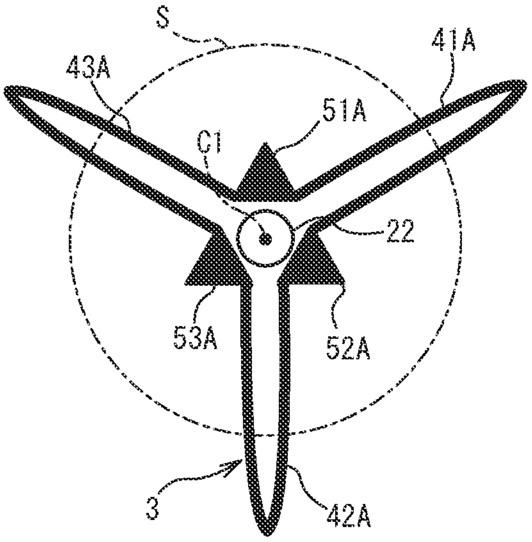
FIG. 3D is views showing the balloon changing shape from the inflated state to the deflated state.

In accordance with the increase in the movement amount of the second portions 51A to 53A toward the center axis C1, as shown in FIG. 3C, the first portions 41A to 43A are pressed outward apart from both the end portions thereof in the circumferential direction E1, and protrude further to the outside than the virtual circle S. As shown in FIG. 3D, the first portions 41A to 43A can be folded in a state in which the second portions 51A to 53A have moved to positions in proximity to the inner tube 22.

Figure 3E:
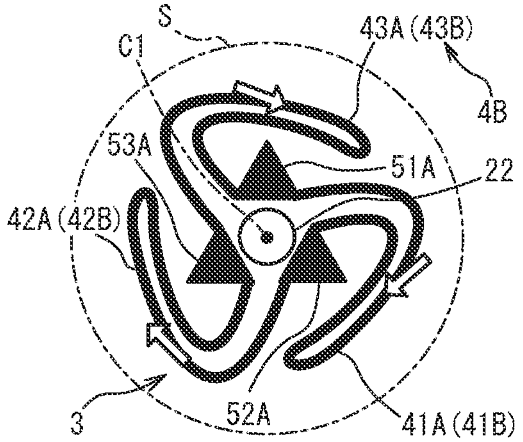
FIG. 3E is views showing the balloon changing shape from the inflated state to the deflated state.

As shown in FIG. 3E, in the folded state, the first portions 41A to 43A cover the second portions 51A to 53A from the outside, and cause the wings 41B to 43B to be formed. In this way, the balloon 3 is in the deflated state.

Operations and Effects

When the balloon 3 changes shape from the inflated state to the deflated state, the second portion 5A for which, in the inflated state, the distance in the radial direction to the center axis C1 is shorter, moves toward the center axis C1 in advance of the first portion 4A. In the process of the second portion 5A moving, the wing 4B is formed by the first portion 4A, and the balloon 3 eventually enters the deflated state. In this case, since the balloon catheter 1A can stabilize the shape of the balloon 3 in the deflated state, the balloon catheter 1A can maintain excellent pass ability through the blood vessel by reducing a diameter of the balloon 3 in the deflated state. Further, even when the balloon 3 repeatedly changes shape between the inflated state and the deflated state, the balloon 3 always folds into the stable shape. Thus, the balloon catheter 1A can reduce the diameter of the balloon 3 in the deflated state.

Note that when the balloon 3 is manufactured by the blow molding, the application of local pressure to portion corresponding to the inflatable portion 3B can be suppressed by the second portion 5A. As a result, it is possible to inhibit the balloon 3 from bursting during the manufacturing process.

The first portion 4A and the second portion 5A of the balloon 3 are provided at the distal end connecting portion 3A, the inflatable portion 3B, and the proximal end connecting portion 3C. In this case, when changing shape from inflated state to the deflated state, at the portions of each of the distal end connecting portion 3A, the inflatable portion 3B, and the proximal end connecting portion 3C, the balloon catheter 1A can move the second portion 5A toward the center axis C1 first. In this case, at each of the distal end connecting portion 3A, the inflatable portion 3B, and the proximal end connecting portion 3C, the balloon 3 can fold into the stable shape. Thus, a diameter of the balloon 3 in the deflated state can be reduced over the whole region thereof in the extending direction. Further, since the possibility is reduced of the diameter increasing when the distal end connecting portion 3A and the proximal end connecting portion 3C are in the folded state, it is possible to improve the passability of the balloon 3 through the blood vessel.

The recess amount of the indentations 51B to 53B formed in the process of the balloon 3 changing shape from the inflated state to the deflated state is larger at the inflatable portion 3B than at the distal end connecting portion 3A and the proximal end connecting portion 3C. Thus, when being deflated, the balloon 3 can shorten a time required to fold the inflatable portion 3B having the larger diameter. Further, since the wings 41B to 43B are smoothly formed, the folded shape of the balloon 3 can be stabilized.

The second portion 5A have a higher rigidity than the first portion 4A. In this case, when the balloon 3 changes shape from the inflated state to the deflated state, a force causing the second portion 5A to move toward the center axis C1 in advance of the first portion 4A operates more easily. Thus, the balloon 3 can realize the configuration in which the second portion 5A moves toward the center axis C1 first, by adjusting a magnitude correlation between the rigidity of the first portion 4A and the second portion 5A.

Further, a behavior that tries to widen the balloon 3 in the deflated state to the outside in the radial direction can be suppressed by the second portion 5A having the higher rigidity. As a result, even when the balloon 3 repeatedly changes shape between the inflated state and the deflated state, the wing 4B can be formed in the stable manner by the first portion 4A. Thus, the diameter of the balloon 3 in the deflated state is stably maintained in the reduced state, and the wing 4B can be suppressed from adopting a flat folded shape.

In the balloon 3, a rigidity of the second portion 5A is higher than that of the first portion 4A, and the second portion 5A are provided over the whole region of the balloon 3 from the distal end portion 3D to the proximal end portion 3P. In this case, when the balloon 3 in the deflated state is inserted into the blood vessel, the second portion 5A fulfill a role of a tension rod. Thus, the balloon catheter 1A can suppress the distal end connecting portion 3A and the proximal end connecting portion 3C from widening in the radial direction when balloon 3 deflates along the extending direction.

The thickness T21 of the second portion 5A is larger than the thickness T11 of the first portion 4A. In this case, the speed at which the second portion 5A moves toward the center axis C1 when the balloon 3 changes shape from the inflated state to the deflated state is slow immediately after the start of the movement, and thereafter becomes faster. Thus, the balloon catheter 1A can fold the balloon 3 in the stable manner using the second portion 5A.

In the inflated state, the distance D21 between the inner surface 501 of the second portion 5A and the center axis C1 is shorter than the distance D11 between the inner surface 401 of the first portion 4A and the center axis C1, apart from the portions at both the end portions of the first portion 4A in the circumferential direction E1. In other words, the inner surface 501 of the second portion 5A is disposed at a position closer to the center axis C1 than the inner surface 401 of the first portion 4A. Further, in the inflated state, the distance D22 from the outer surface 502 of the second portion 5A to the center axis C1 is longer than the distance D12 from the outer surface 402 of the first portion 4A to the center axis C1. In these cases, when the balloon 3 changes shape from the inflated state to the deflated state, the second portion 5A more easily move toward the center axis C1 in advance of the first portion 4A. Thus, even when the balloon 3 repeatedly changes shape between the inflated state and the deflated state, the balloon 3 can always be folded into the stable shape.

In the inflated state, the distance D22 is longer than the distance D12, and thus, the outer surface 502 of the second portion 5A protrudes further to the outside than the outer surface 402 of the first portion 4A. In this case, when the balloon 3 is caused to be in the inflated state inside the blood vessel, the second portion 5A easily comes into contact with the inner wall of the blood vessel. Thus, the balloon catheter 1A can cause the second portion 5A of the balloon 3 to act on the blood vessel in a favorable manner.

The second portions 51A to 53A are disposed at the equal intervals in the circumferential direction E1. In this case, when the balloon 3 changes shape from the inflated state to the deflated state, the wings 41B to 43B formed by the first portions 41A to 43A can be caused to have a uniform size. Thus, the balloon catheter 1A can uniformly deflate the balloon 3 in the circumferential direction E1.

The shape of the balloon 3 is remembered in the state in which the indentations 51B to 53B recessed toward the center axis C1 are formed by the second portions 51A to 53A. In this case, when the balloon 3 changes shape from the inflated state to the deflated state, the configuration can be easily realized in which the second portion 5A moves first toward the center axis C1.

The first portion 4A and the second portion 5A of the balloon 3 are configured by the same material. In this case, the balloon catheter 1A can be easily manufactured.

While the invention has been described in conjunction with various example structures outlined above and illustrated in the figures, various alternatives, modifications, variations, improvements, and/or substantial equivalents, whether known or that may be presently unforeseen, may become apparent to those having at least ordinary skill in the art. Accordingly, the example embodiments of the disclosure, as set forth above, are intended to be illustrative of the invention, and not limiting the invention. Various changes may be made without departing from the spirit and scope of the disclosure. Therefore, the disclosure is intended to embrace all known or later developed alternatives, modifications, variations, improvements, and/or substantial equivalents. Some specific examples of potential alternatives, modifications, or variations in the described invention are provided below:

MODIFIED EXAMPLES

The present disclosure is not limited to the above-described embodiment and various modifications are possible. The number of the first portion 4A and the second portion 5A of the balloon 3 is not limited to three, as in the above-described embodiment, and may be another desired number. The first portion 4A and the second portion 5A of the balloon 3 may be formed using different materials. For example, the balloon 3 may be provided with the second portion 5A on the outer surface of a tube-shaped portion that has a tubular shape in the inflated state. In this case, a section of the tube-shaped portion between the two second portions 5A, 5A that are adjacent to each other corresponds to the first portion 4A.

In the above description, when the balloon 3 changes shape from the inflated state to the deflated state, the second portion 5A moves toward the center axis C1 in advance of the first portion 4A. In contrast to this, for example, the second portion 5A may start to move in advance at a time point immediately after the balloon 3 starts to deform from the inflated state to the deflated state, and thereafter, the movement of the first portion 4A toward the center axis C1 may be started. Further, the first portion 4A may start to move in advance, and thereafter, the movement of the second portion 5A toward the center axis C1 may be started.

The first portion 4A and the second portion 5A may be provided only on the inflatable portion 3B of the balloon 3, and need not necessarily be provided on the distal end connecting portion 3A and the proximal end connecting portion 3C. In this case, the second portion 5A need not necessarily extend from the distal end portion 30D to the proximal end portion 30P of the inflatable portion 3B, and may be divided in the extending direction. Further, the first portion 4A and the second portion 5A may be provided on the inflatable portion 3B, and one of the distal end connecting portion 3A and the proximal end connecting portion 3C of the balloon 3.

The second portion 5A may be configured by separate members being a portion further to the inside and a portion further to the outside than the distance D12 in the radial direction. In this case, the portion further to the inside than the distance D12 in the radial direction may be configured by the same material as the first portion 4A, and the portion further to the outside than the distance D12 in the radial direction may be configured by a member different from the first portion 4A. Of the second portion 5A, the portion further to the outside than the distance D12 in the radial direction, may have a higher rigidity than the portion further to the inside than the distance D12 in the radial direction. In other words, the portion of the second portion 5A further to the outside than the distance D12 in the radial direction may form a rigid portion.

The thickness T11 of the first portion 4A may be the same as the thickness T21 of the second portion 5A. In this case, the outer surface 502 of the second portion 5A need not necessarily protrude to the outside with respect to the outer surface 402 of the first portion 4A.

The second portions 51A to 53A need not necessarily be disposed at the equal intervals in the circumferential direction E1. For example, the second portions 51A to 53A may be locally provided at part of the balloon 3 in the circumferential direction E1.

The indentation 5B needs not necessarily be provided in the balloon 3 in the inflated state. In this case, the inner surface of the balloon 3 in the inflated state may be formed in a tube shape without any protrusions or recesses. The first portion 4A and the second portion 5A of the balloon 3 may be formed from different materials. For example, the second portion 5A may be formed by doping a new material forming the first portion 4A.

Balloon Catheter 1B

Figure 4:
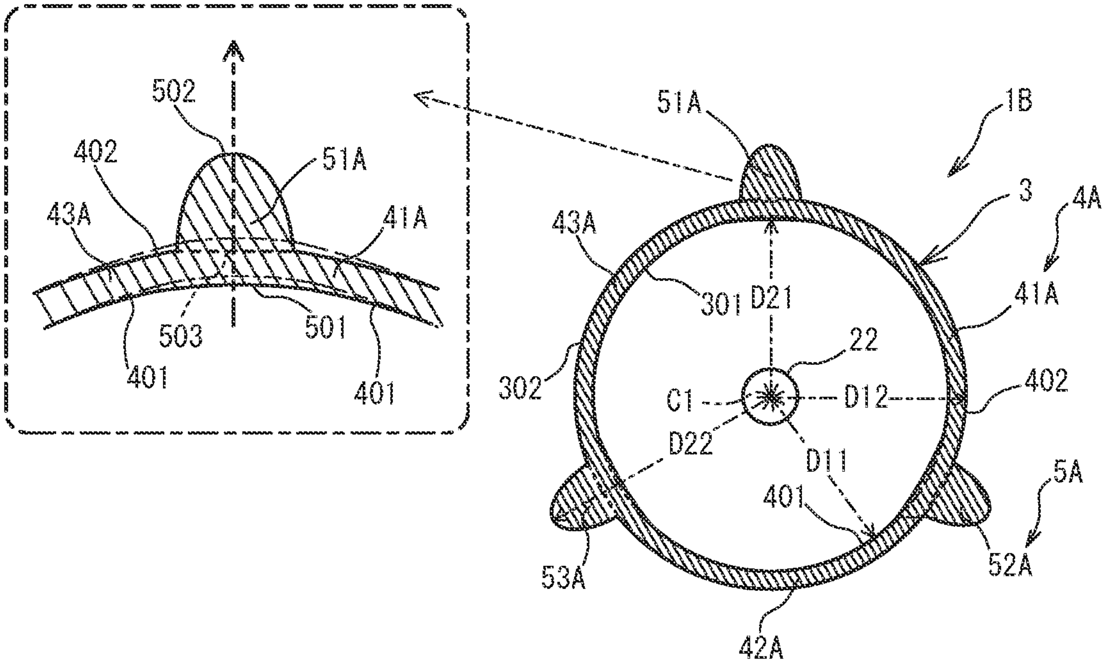
FIG. 4 includes views showing the balloon in a balloon catheter.

As in the balloon 3 of a balloon catheter 1B shown in FIG. 4, the outer surface 502 of each of the second portions 51A to 53A may have a rounded shape. In this case, when the balloon 3 passes through the blood vessel, it is possible to suppress the second portion 5A from becoming caught on the inner wall of the blood vessel. Thus, the balloon catheter 1B can secure the excellent passability of the balloon 3 through the blood vessel.

Note that the shape of the outer surface 502 of the second portion 5A is not limited to the above shape, and it goes without saying that various shapes may be adopted in accordance with an application or a function.

Balloon Catheter 1C

Figure 5:
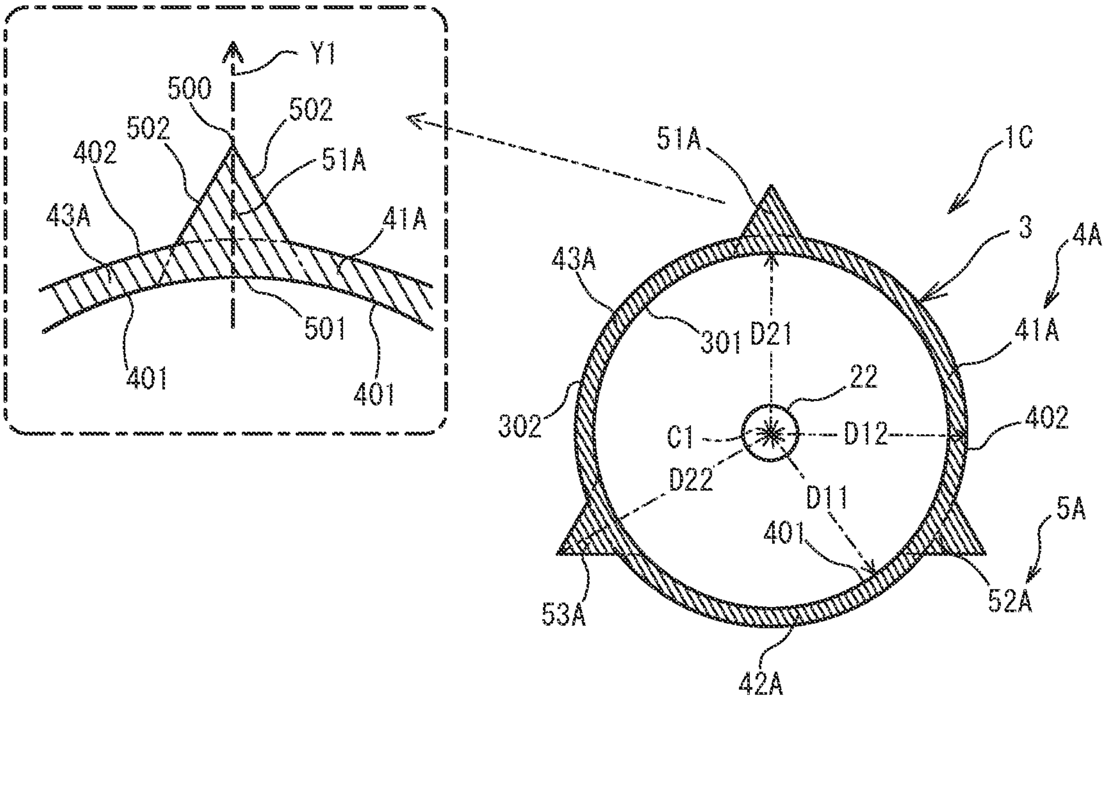
FIG. 5 includes views showing the balloon in a balloon catheter.

As in the balloon 3 of a balloon catheter 1C shown in FIG. 5, in the inflated state, the distance D11 between the inner surface 401 of the first portion 4A and the center axis C1, and the distance D21 between the inner surface 501 of the second portion 5A and the center axis C1 may be the same as each other. In this case, no step is formed in the inner surface 301 of the balloon 3, and the inner surfaces 401 and 501 form a true circle in cross section.

Balloon Catheter 1D

Figure 6:
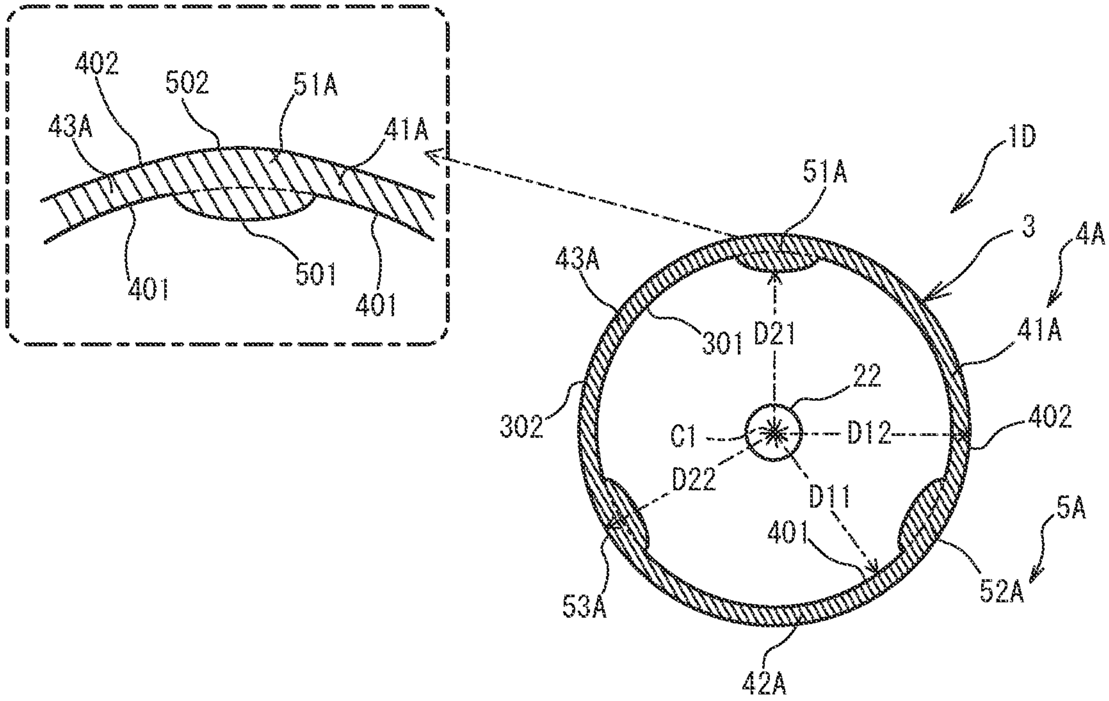
FIG. 6 includes views showing the balloon in a balloon catheter.

As in the balloon 3 of a balloon catheter 1D shown in FIG. 6, in the inflated state, the distance D12 between outer surface 402 of the first portion 4A and the center axis C1 may be the same as the distance D22 between the outer surface 502 of the second portion 5A and the center axis C1. In this case, no step is formed in the outer surface 302 of the balloon 3, and the outer surfaces 402 and 502 form a true circle in cross section. Further, a step protruding to the inside is formed in the inner surface 301 of the balloon 3 at a portion corresponding to the inner surface 501 of the second portion 5A.

Balloon Catheter 1E

Figure 7:
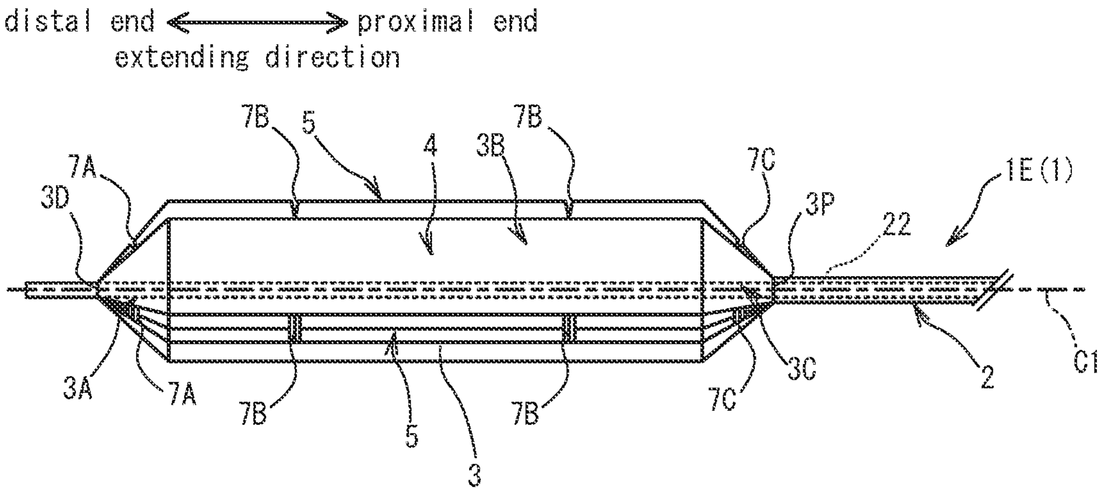
FIG. 7 is a view showing a balloon catheter.

As in the balloon 3 of a balloon catheter 1E shown in FIG. 7, a slit 7A may be provided in the second portion 5A disposed at the distal end connecting portion 3A, two slits 7B may be provided in the second portion 5A disposed at the inflatable portion 3B, and a slit 7C may be provided in the second portion 5A disposed at the proximal end connecting portion 3C. The slits 7A to 7C are cuts or cut out portions extending toward the center axis C1 from the outer surface 502 of the second portion 5A.

The slit 7A provided in the second portion 5A disposed at the distal end connecting portion 3A can maintain the flexibility of the distal end connecting portion 3A while suppressing the distal end connecting portion 3A from widening in the deflated state. Thus, the balloon catheter 1E can improve the passability of the balloon 3 through the blood vessel when the balloon 3 is inserted into the blood vessel in the deflated state.

The slit 7C provided in the second portion 5A disposed at the distal end connecting portion 3A can maintain the flexibility of the proximal end connecting portion 3C while suppressing the proximal end connecting portion 3C from widening in the deflated state. Thus, the balloon catheter 1E can improve the passability of the balloon 3 through the blood vessel when the balloon 3 is pulled out from the blood vessel in the deflated state.

The two slits 7B provided in the second portion 5A disposed at the inflatable portion 3B can suppress the inflatable portion 3B from widening in the deflated state. Further, since the second portion 5A disposed at the inflatable portion 3B does not stick out inside a curved blood vessel, it is possible to improve trackability in a curved blood vessel.

Note that it is preferable for bottom portions of the slits 7A to 7C, that is, portions of the slits 7A to 7C closest to the center axis C1, to be disposed the outside in the radial direction with respect to the bottom surface 503 (refer to FIG. 1) of the second portion 5A. In this way, when inserting the balloon 3 in the deflated state into the blood vessel, it is possible to effectively deploy the role of the second portion 5A as the tension rod. Only some of the slits 7A, 7B, and 7C shown in FIG. 7 may be provided in the second portion 5A. For example, the slits 7B may be provided in only the second portion 5A of the inflatable portion 3B of the balloon 3, and the slits 7A and 7C need not necessarily be provided in the second portion 5A of the distal end connecting portion 3A and the proximal end connecting portion 3C.

Balloon Catheter 1F

FIG. 8 show a process of the balloon 3 of a balloon catheter 1F changing shape from the inflated state to the deflated state. It is assumed that the compressed fluid is removed from the balloon 3 in the inflated state shown in FIG. 8A. The balloon 3 changes shape from the inflated state to the deflated state in accordance with the removal of the compressed fluid.

Figure 8A:
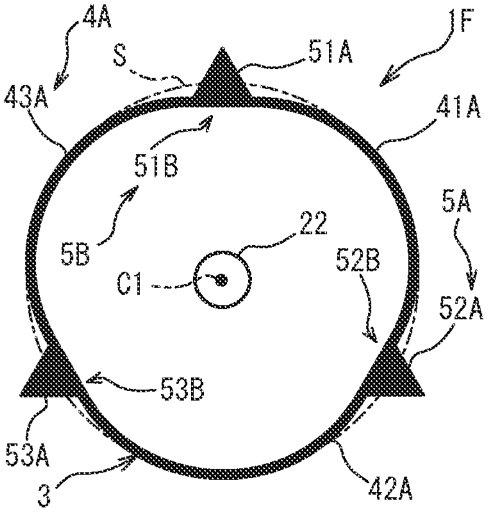
FIG. 8A is a view showing the balloon of a balloon catheter changing shape from the inflated state to the deflated state.
Figure 8B:
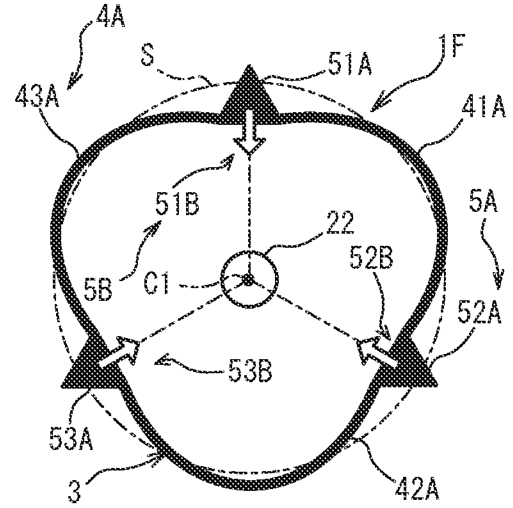
FIG. 8B is a view showing the balloon of a balloon catheter changing shape from the inflated state to the deflated state.
Figure 8C:
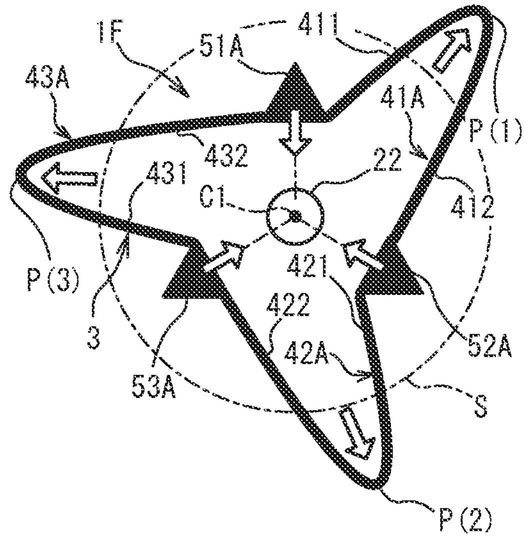
FIG. 8C is a view showing the balloon of a balloon catheter changing shape from the inflated state to the deflated state.

As shown in FIG. 8B, in the process of the balloon 3 changing shape from the inflated state to the deflated state, the second portions 51A to 53A move toward the center axis C1 in advance of the first portions 41A to 43A. Apart from portions at both the end portions thereof in the circumferential direction E1 (refer to FIG. 1), the first portions 41A to 43A are pushed to the outside and protrude to the outside of the virtual circle S. As shown in FIG. 8C, the curvature of the first portion 41A is greatest at an apex P (1). The curvature of the first portion 42A is greatest at an apex P (2). The curvature of the first portion 43A is greatest at an apex P (3).

Figure 9:
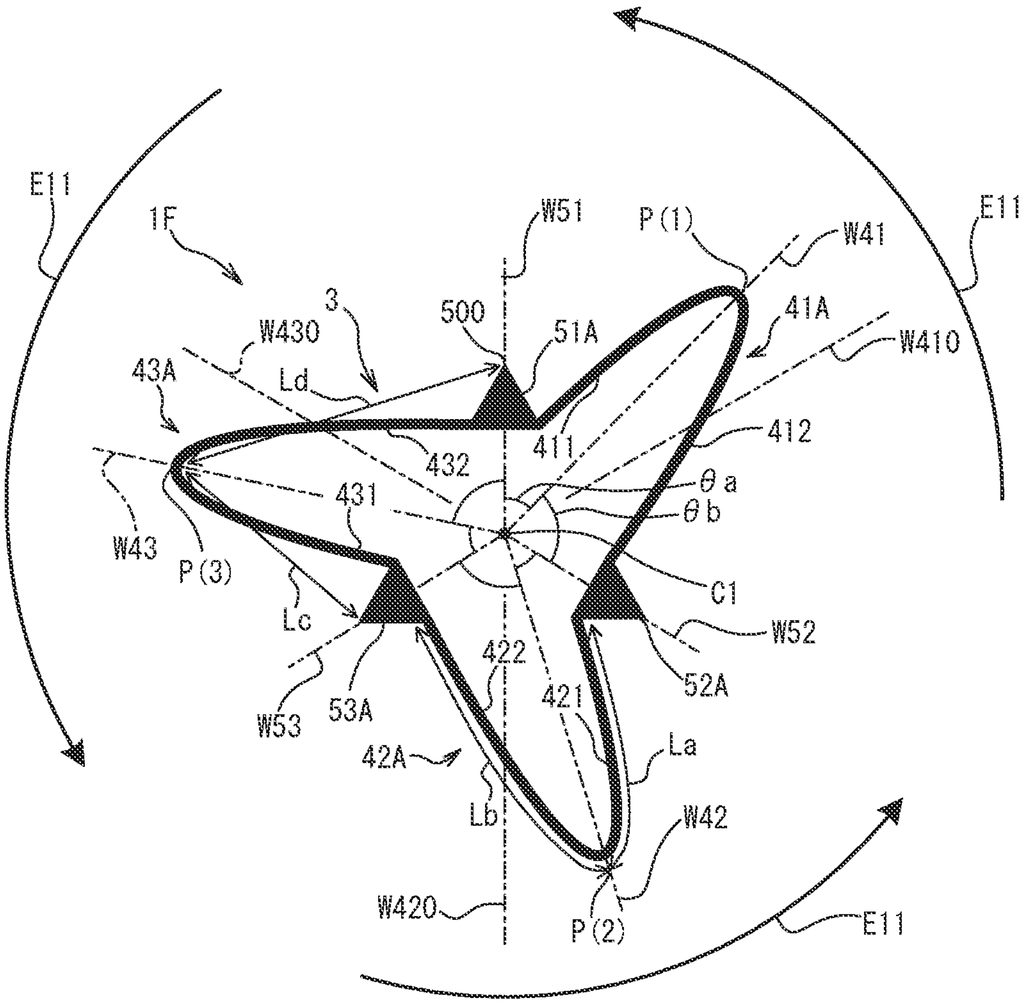
FIG. 9 is a view showing the balloon of the balloon catheter in the deflated state.

As shown in FIG. 9, a virtual plane extending in the radial direction from the center axis C1 and passing through the apex P (1) of the first portion 41A is denoted by W41. A virtual plane extending in the radial direction from the center axis C1 and passing through the apex P (2) of the first portion 42A is denoted by W42. A virtual plane extending in the radial direction from the center axis C1 and passing through the apex P (3) of the first portion 43A is denoted by W43. A virtual plane extending in the radial direction from the center axis C1 and passing through the apex 500 of the second portion 51A is denoted by W51. A virtual plane extending in the radial direction from the center axis C1 and passing through the apex 500 of the second portion 52A is denoted by W52. A virtual plane extending in the radial direction from the center axis C1 and passing through the apex 500 of the second portion 53A is denoted by W53.

A virtual plane for which a distance to each of the planes W51 and W52 is equal, that is a virtual plane equally dividing the angle formed between the planes W51 and W52, is denoted by a plane W410. A virtual plane for which a distance to each of the planes W52 and W53 is equal, that is a virtual plane equally dividing the angle formed between the planes W52 and W53, is denoted by a plane W420. A virtual plane for which a distance to each of the planes W53 and W51 is equal, that is a virtual plane equally dividing the angle formed between the planes W53 and W51, is denoted by a plane W430. Of the circumferential direction E1 (refer to FIG. 1), a counterclockwise direction side in FIG. 9 will be referred to as one side E11 of the circumferential direction E1.

The angle formed between the planes W51 and W41 is the same as the angle formed between the planes W52 and W42, and as the angle formed between the plans W53 and W43. Hereinafter, this angle will be denoted by θa. The angle formed between the planes W41 and W52 is the same as the angle formed between the planes W42 and W53, and as the angle formed between the planes W43 and W51. Hereinafter, this angle will be denoted by θb. In this case, the angle θb is larger than the angle θa (θa<θb). In other words, the apex P (1) is disposed at the one side E11 of the circumferential direction E1 with respect to the plane W410. The apex P (2) is disposed at the one side E11 of the circumferential direction E1 with respect to the plane W420. The apex P (3) is disposed at the one side E11 of the circumferential direction E1 with respect to the plane W430.

Note that in FIG. 9, only the angle θa formed between the planes W51 and W41 is shown, and the angle θa between the planes W52 and W42, and the angle θa formed between the planes W53 and W43 are omitted. Further, only the angle θb formed between the planes W41 and W52 is shown, and the angle θb between the planes W42 and W53, and the angle θb formed between the planes W43 and W51 are omitted.

Of the first portion 41A, a portion from a connection portion with the second portion 51A to the apex P (1) will be referred to as a first extending portion 411. Of the first portion 41A, a portion from a connection portion with the second portion 52A to the apex P (1) will be referred to as a second extending portion 412. Of the first portion 42A, a portion from a connection portion with the second portion 52A to the apex P (2) will be referred to as a first extending portion 421. Of the first portion 42A, a portion from a connection portion with the second portion 53A to the apex P (2) will be referred to as a second extending portion 422. Of the first portion 43A, a portion from a connection portion with the second portion 53A to the apex P (3) will be referred to as a first extending portion 431. Of the first portion 43A, a portion from a connection portion with the second portion 51A to the apex P (3) will be referred to as a second extending portion 432.

The lengths of the first extending portions 411, 421, and 431 are the same as each other. Hereinafter, this length will be denoted by La. Further, the lengths of the second extending portions 412, 422, and 432 are the same as each other. Hereinafter, this length will be denoted by Lb. In this case, the length Lb is longer than the length La (La<Lb). Note that in FIG. 9, only the length La of the first extending portion 421 is shown, and the lengths La of the first extending portions 411 and 431 are omitted. Further, only the length Lb of the second extending portion 422 is shown, and the lengths Lb of the second extending portions 412 and 432 are omitted.

A distance between the apex P (1) of the first portion 41A and the apex 500 of the second portion 51A, a distance between the apex P (2) of the first portion 42A and the apex 500 of the second portion 52A, and a distance between the apex P (3) of the first portion 43A and the apex 500 of the second portion 53A are the same as each other. Hereinafter, this distance will be denoted by Lc. A distance between the apex P (1) of the first portion 41A and the apex 500 of the second portion 52A, a distance between the apex P (2) of the first portion 42A and the apex 500 of the second portion 53A, and a distance between the apex P (3) of the first portion 43A and the apex 500 of the second portion 51A are the same as each other. Hereinafter, this distance will be denoted by Ld. In this case, the length Ld is longer than the length Lc (Lc<Ld).

Note that in FIG. 9, only the distance Lc between the apex P (3) of the first portion 43A and the apex 500 of the second portion 53A is shown, and the length Lc between the apex P (1) of the first portion 41A and the apex 500 of the second portion 51A, and the length Lc between the apex P (2) of the first portion 42A and the apex 500 of the second portion 52A are omitted. Further, only the distance Ld between the apex P (3) of the first portion 43A and the apex 500 of the second portion 51A is shown, and the length Ld between the apex P (1) of the first portion 41A and the apex 500 of the second portion 52A, and the length Ld between the apex P (2) of the first portion 42A and the apex 500 of the second portion 53A are omitted.

Figure 8D:
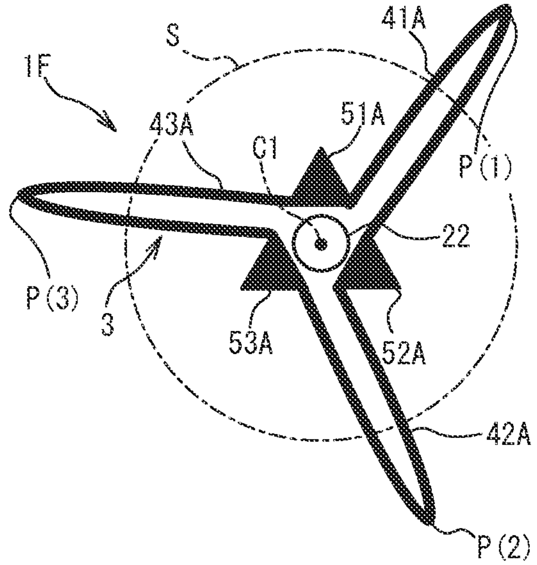
FIG. 8D is a view showing the balloon of a balloon catheter changing shape from the inflated state to the deflated state.

As shown in FIG. 8D, the first portions 41A to 43A are folded in a state in which the second portions 51A to 53A have moved to a position in the vicinity of the inner tube 22. In this state also, the relationship between the lengths La and Lb (La<Lb), the relationship between the lengths Lc and Ld (Lc<Ld), and the relationship between the angles θa and θb (θa<θb) described with reference to FIG. 9 are maintained.

Figure 8E:
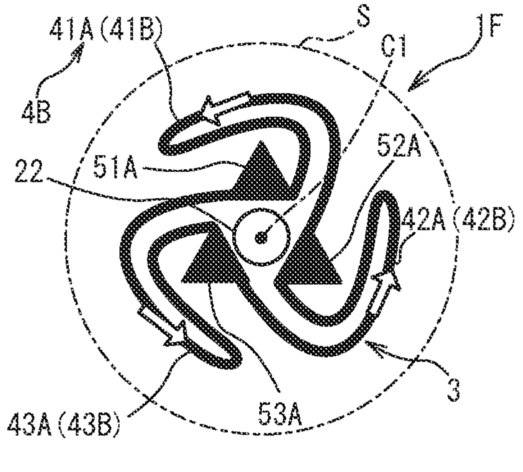
FIG. 8E is a view showing the balloon of a balloon catheter changing shape from the inflated state to the deflated state.

As shown in FIG. 8E, the first portions 41A to 43A in the folded state cover the second portions 51A to 53A from the outside, and form the wings 41B to 43B. In this way, the balloon 3 is in the deflated state.

Here, the length Lb of the second extending portion 412 is longer than the length La of the first extending portion 411 of the first portion 41A (La<Lb). The length Ld between the apex P (1) of the first portion 41A to the apex 500 of the second portion 52A is longer than the distance Lc between the apex P (1) of the first portion 41A and the apex 500 of the second portion 51A (Lc<Ld). The apex P (1) is disposed to the one side E11 of the circumferential direction E1 with respect to the plane W410. Thus, when the balloon 3 changes shape from the inflated state to the deflated state, the first portion 41A is easily disposed at a position in the vicinity of the second portion 51A adjacent on the one side E11 of the circumferential direction E1. Similarly, the first portion 42A is easily disposed at a position in the vicinity of the second portion 52A adjacent on the one side E11 of the circumferential direction E1. The first portion 43A is easily disposed at a position in the vicinity of the second portion 53A adjacent on the one side E11 of the circumferential direction E1.

Thus, in the balloon catheter 1F, in the process of the balloon 3 changing shape from the inflated state to the deflated state, the position of the first portion 4A is stabilized, and is easily disposed at the position covering the second portion 5A. Thus, in the process of the balloon 3 changing shape from the inflated state to the deflated state, the first portion 4A can easily cover the second portion 5A that is adjacent on the one side E11 of the circumferential direction E1. Further, even when the balloon 3 repeatedly changes shape between the inflated state and the deflated state, the balloon catheter 1F can appropriately cover the second portion 5A using the first portion 4A in the deflated state.

Balloon Catheter 1G

Figure 10A:
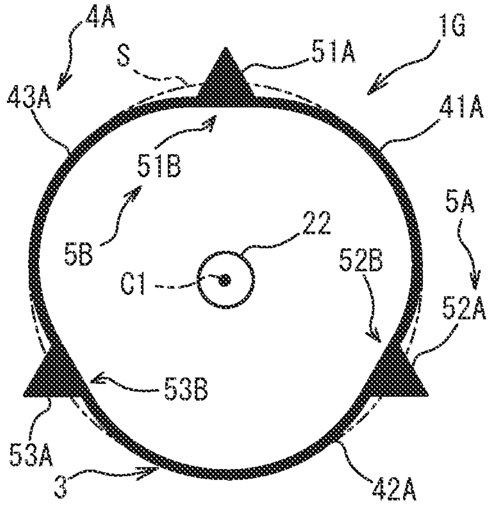
FIG. 10A is a view showing the balloon of a balloon catheter changing shape from the inflated state to the deflated state.
Figure 10B:
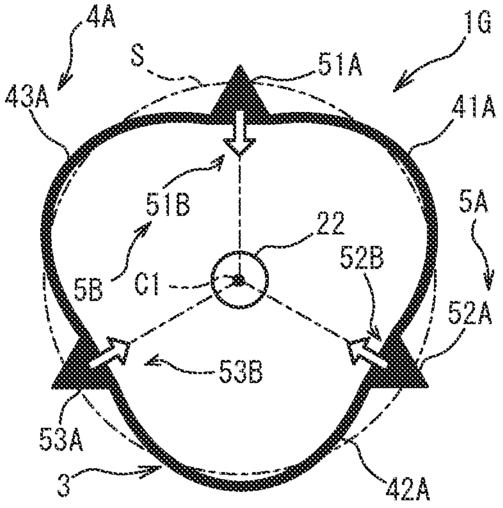
FIG. 10B is a view showing the balloon of a balloon catheter changing shape from the inflated state to the deflated state.

A balloon catheter 1G differs from the balloon catheter 1F in that the shape of the first portions 41A, 42A, and 43A differs in the process of the balloon 3 changing shape from the inflated state to the deflated state. FIG. 10A to FIG. 10E show the process of the balloon 3 of the balloon catheter 1G changing shape from the inflated state to the deflated state. States shown in FIG. 10A and FIG. 10B are the same as the states shown in FIG. 8A and FIG. 8B.

Figure 10C:
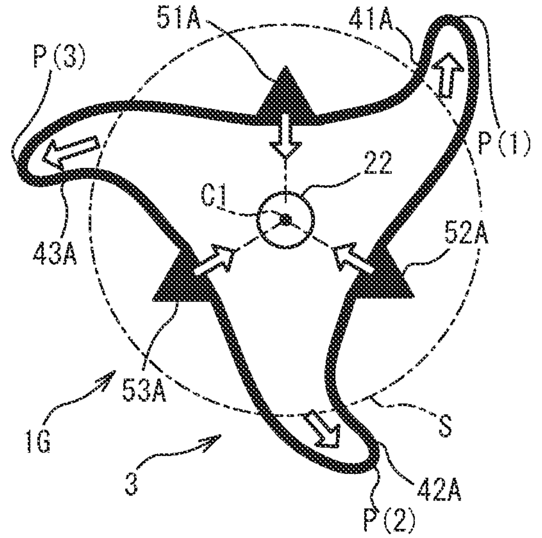
FIG. 10C is a view showing the balloon of a balloon catheter changing shape from the inflated state to the deflated state.

In the process of the balloon 3 changing shape from the inflated state to the deflated state, the first portions 41A to 43A are pushed to the outside, and protrude to the outside of the virtual circle S. As shown in FIG. 10C, the curvature of the first portion 41A is greatest at the apex P (1). The curvature of the first portion 42A is greatest at the apex P (2). The curvature of the first portion 43A is greatest at the apex P (3). In the balloon 3, the relationship between the lengths La and Lb (La<Lb), and the relationship between the lengths Lc and Ld (Lc<Ld) (refer to FIG. 11) are the same as in the balloon catheter 1F (refer to FIG. 9). Further, the positional relationship between the plane W410 and the apex P (1), the positional relationship between the plane W420 and the apex P (2), and the positional relationship between the plane W430 and the apex P (3) (refer to FIG. 11) are also the same as those of the balloon catheter 1F (refer to FIG. 9).

Figure 11:
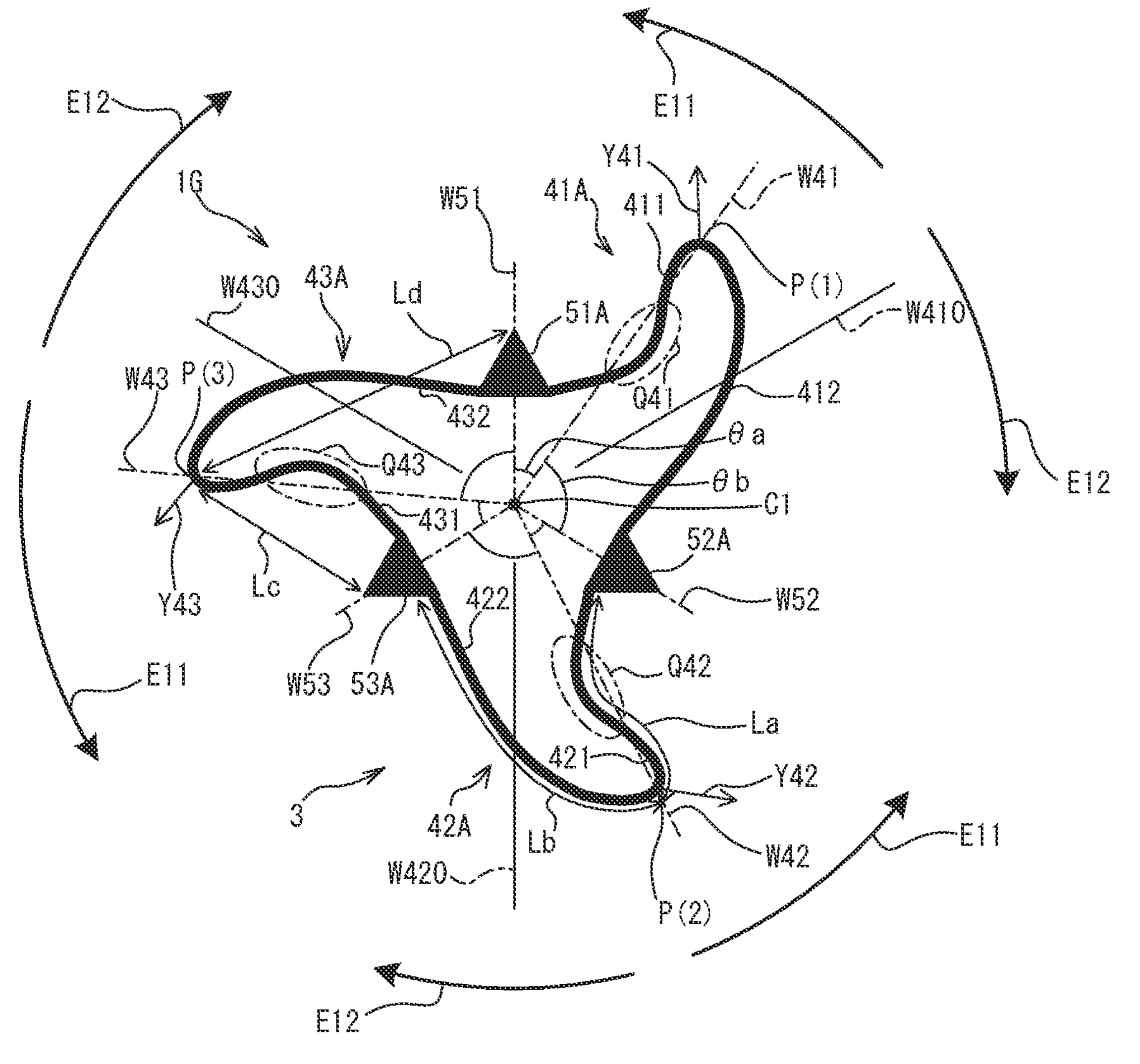
FIG. 11 is a view showing the balloon of the balloon catheter in the deflated state.

As shown in FIG. 11, a portion (a portion inside a frame line Q41) of the first extending portion 411 of the first portion 41A is disposed on a side (hereinafter referred to as the other side E12 of the circumferential direction E1) opposite to the one side E11 of the circumferential direction E1 (refer to FIG. 1) with respect to the plane W41, that is, is disposed on the side of the second portion 52A with respect to the plane W41. A portion (a portion inside a frame line Q42) of the first extending portion 421 of the first portion 42A is disposed on the other side E12 of the circumferential direction E1 with respect to the plane W42, that is, is disposed on the side of the second portion 53A with respect to the plane W42. A portion (a portion inside a frame line Q43) of the first extending portion 431 of the first portion 43A is disposed on the other side E12 of the circumferential direction E1 with respect to the plane W43, that is, is disposed on the side of the second portion 51A with respect to the plane W43.

A direction Y41 is defined that is perpendicular to a tangent line of the first portion 41A at the apex P (1) of the first portion 41A and extends to the outside of the balloon 3. In relation to the radial direction centered on the center axis C1, the direction Y41 extends obliquely toward the one side E11 of the circumferential direction E1. A direction Y42 is defined that is perpendicular to a tangent line of the first portion 42A at the apex P (2) of the first portion 42A and extends to the outside of the balloon 3. In relation to the radial direction centered on the center axis C1, the direction Y42 extends obliquely toward the one side E11 of the circumferential direction E1. A direction Y43 is defined that is perpendicular to a tangent line of the first portion 43A at the apex P (3) of the first portion 43A and extends to the outside of the balloon 3. In relation to the radial direction centered on the center axis C1, the direction Y43 extends obliquely toward the one side E11 of the circumferential direction E1.

Figure 10D:
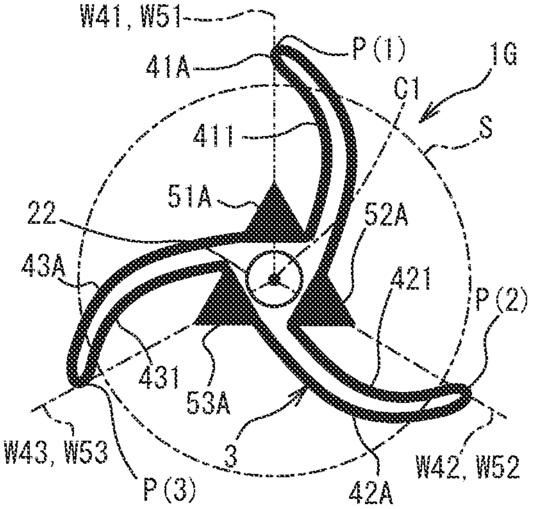
FIG. 10D is a view showing the balloon of a balloon catheter changing shape from the inflated state to the deflated state.

As shown in FIG. 10D, the first portions 41A to 43A are folded in a state in which the second portions 51A to 53A have moved to a position in the vicinity of the inner tube 22. The relationship between the lengths La and Lb (La<Lb) and the relationship between the distances Lc and Ld (Lc<Ld) described with reference to FIG. 11 are maintained in this state also. On the other hand, in FIG. 10D, the planes W41 and W51 are aligned, the planes W42 and W52 are aligned, and planes W43 and W53 are aligned.

The whole region of the first extending portion 411 of the first portion 41A is disposed on the other side E12 (refer to FIG. 11) of the circumferential direction E1 with respect to the plane W41. The whole region of the first extending portion 421 of the first portion 42A is disposed on the other side E12 of the circumferential direction E1 with respect to the plane W42. The whole region of the first extending portion 431 of the first portion 43A is disposed on the other side E12 of the circumferential direction E1 with respect to the plane W43. Each of the directions Y41, Y42, and Y43 (refer to FIG. 11) is inclined to the one side E11 (refer to FIG. 11) of the circumferential direction E1, with respect to the radial direction.

Figure 10E:
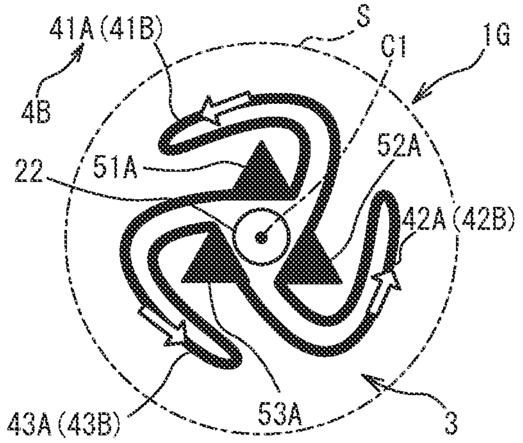

As shown in FIG. 10E, in the folded state, the first portions 41A to 43A cover the second portions 51A to 53A from the outside and cause the wings 41B to 43B to be formed. In this way, the balloon 3 is in the deflated state.

Here, the apex P (1) of the first portion 41A is disposed on the one side E11 of the circumferential direction E1 with respect to the plane W410. Further, a portion of the first extending portion 411 is disposed on the other side E12 of the circumferential direction E1 with respect to the plane W41, and the direction Y41 is inclined to the one side E11 of the circumferential direction E1 with respect to the plane W41. Thus, when the balloon 3 changes shape from the inflated state to the deflated state, the first portion 41A is easily disposed at a position in the vicinity of the second portion 51A that is adjacent on the one side E11 of the circumferential direction E1, and easily covers the second portion 51A from the outside in the radial direction. Similarly, the first portion 42A is easily disposed at a position in the vicinity of the second portion 52A that is adjacent on the one side E11 of the circumferential direction E1, and easily covers the second portion 52A from the outside in the radial direction. The first portion 43A is easily disposed at a position in the vicinity of the second portion 53A that is adjacent on the one side E11 of the circumferential direction E1, and easily covers the second portion 53A from the outside in the radial direction.

In other words, in the balloon catheter 1G, the position of the first portion 4A is stable in the process of the balloon 3 changing shape from the inflated state to the deflated state, and the first portion 4A is easily disposed at the position covering the second portion 5A that is adjacent thereto on the one side E11 of the circumferential direction E1. Further, in the balloon catheter 1G, in the process of the balloon 3 changing shape from the inflated state to the deflated state, the first portion 4A has the shape to easily cover the second portion 5A from the outside in the radial direction. Thus, using the first portion 4A, the balloon catheter 1G can easily cover the second portion 5A that is adjacent to the first portion 4A on the one side E11 of the circumferential direction E1 with respect to the first portion 4A. Further, the balloon catheter 1G can appropriately cover the second portion 5A using the first portion 4A in the deflated state, even when the balloon 3 repeatedly changes shape between the inflated state and the deflated state.

Special Notes Relating to Balloon Catheters 1F and 1G

The lengths of the first extending portions 411, 421, and 431 may be different from each other. The lengths of the second extending portions 412, 422, and 432 may be different from each other. In this case, in the first portion 41A, it is sufficient that the second extending portion 412 be longer than the first extending portion 411. In the first portion 42A, it is sufficient that the second extending portion 422 be longer than the first extending portion 421. In the first portion 43A, it is sufficient that the second extending portion 432 be longer than the first extending portion 431.

The distance between the apex P (1) of the first portion 41A and the apex 500 of the second portion 51A, the distance between the apex P (2) of the first portion 42A and the apex 500 of the second portion 52A, and the distance between the apex P (3) of the first portion 43A and the apex 500 of the second portion 53A may be different from each other. The distance between the apex P (1) of the first portion 41A and the apex 500 of the second portion 52A, the distance between the apex P (2) of the first portion 42A and the apex 500 of the second portion 53A, and the distance between the apex P (3) of the first portion 43A and the apex 500 of the second portion 51A may be different from each other. In this case, it is sufficient that the distance between the apex P (1) of the first portion 41A and the apex 500 of the second portion 52A be longer than the distance between the apex P (1) of the first portion 41A and the apex 500 of the second portion 51A. It is sufficient that the distance between the apex P (2) of the first portion 42A and the apex 500 of the second portion 53A be longer than the distance between the apex P (2) of the first portion 42A and the apex 500 of the second portion 52A. It is sufficient that the distance between the apex P (3) of the first portion 43A and the apex 500 of the second portion 51A be longer than the distance between the apex P (3) of the first portion 43A and the apex 500 of the second portion 53A.

What is claimed is:

1. A balloon for a catheter capable of being in an inflated state and a deflated state in accordance with changes in internal pressure, the balloon for a catheter comprising:

an inflatable portion configured to, in a process of changing shape from the deflated state to the inflated state, inflate by moving to the outside in a radial direction centered on a center axis extending in a predetermined extending direction, and to form a tube shape extending in the extending direction in the inflated state;

a distal end connecting portion being a portion extending from a distal end portion of the inflatable portion, the distal end portion being an end portion on one side of the inflatable portion in the extending direction, and, in the inflated state, a diameter of the distal end connecting portion at one end portion being larger than a diameter at an other end portion, the one end portion being an end portion connected to the inflatable portion, and the other end portion being an end portion on an opposite side to the one end portion; and a proximal end connecting portion being a portion extending from a proximal end portion of the inflatable portion, the proximal end portion being an end portion on an other side of the inflatable portion in the extending direction, and, in the inflated state, a diameter of the proximal end connecting portion at one end portion of the proximal end connecting portion being larger than a diameter of an other end portion of the proximal end connecting portion, the one end portion being an end portion connected to the inflatable portion, and the other end portion being an end portion on an opposite side to the one end portion, wherein:

at least the inflatable portion includes:

a plurality of first portions forming wings in the deflated state, and a plurality of second portions adjacent to and formed integrally with the plurality of first portions in a circumferential direction centered on the center axis, in the inflated state, the plurality of second portions encompassing all portions of the inflatable portion other than the plurality of first portions, and in the inflated state, each of the plurality of first portions curves in a circular arc shape centered on the center axis, and a distance, in the radial direction, from the center axis to each of the plurality of second portions is shorter than a distance, in the radial direction, from the center axis to each of the plurality of first portions, and each of the plurality of second portions has a higher rigidity than that of the plurality of first portions.

2. The balloon for a catheter according to claim 1, wherein the plurality of second portions causes formation of indentations recessed toward the center axis, by moving toward the center axis in advance of the plurality of first portions, in the process of changing shape from the inflated state to the deflated state.

3. The balloon for a catheter according to claim 2, wherein the distal end connecting portion and the proximal end connecting portion each include the plurality of first portions and the plurality of second portions, each of the plurality of first portions and plurality of second portions extend from the other end portion of the distal end connecting portion to the other end portion of the proximal end connecting portion in the extending direction, and an amount of the indentations formed in the process of changing shape from the inflated state to the deflated state is larger at the inflatable portion than at the distal end connecting portion and the proximal end connecting portion.

4. The balloon for a catheter according to claim 2, wherein a shape in which the indentations recessed toward the center axis are formed by the plurality of second portions is remembered.

5. The balloon for a catheter according to claim 1, wherein the distal end connecting portion and the proximal end connecting portion each include the plurality of first portions and the plurality of second portions, and each of the plurality of first portions and the plurality of second portions extend from the other end portion of the distal end connecting portion to the other end portion of the proximal end connecting portion in the extending direction.

6. The balloon for a catheter according to claim 5, wherein of the plurality of second portions, at least one slit is provided at a portion disposed at the distal end connecting portion.

7. The balloon for a catheter according to claim 5, wherein of the plurality of second portions, at least one slit is provided at a portion disposed at the proximal end connecting portion.

8. The balloon for a catheter according to claim 1, wherein a thickness, in the radial direction, of each of the plurality of second portions is larger than a thickness, in the radial direction, of each of the plurality of first portions.

9. The balloon for a catheter according to claim 8, wherein in the inflated state, a distance between an inner surface of the plurality of second portions and the center axis is shorter than a distance between an inner surface of the plurality of first portions and the center axis.

10. The balloon for a catheter according to claim 8, wherein in the inflated state, a distance between an outer surface of the plurality of second portions and the center axis is longer than a distance between an outer surface of the plurality of first portions and the center axis.

11. The balloon for a catheter according to claim 1, wherein an outer surface of the plurality of second portions has a rounded shape.

12. The balloon for a catheter according to claim 1, wherein the plurality of second portions is disposed at equal intervals in the circumferential direction.

13. The balloon for a catheter according to claim 1, wherein the plurality of first portions and the plurality of second portions are formed from the same material.

14. The balloon for a catheter according to claim 1, wherein of the plurality of second portions, at least one slit is provided at a portion disposed at the inflatable portion.

15. The balloon for a catheter according to claim 1, wherein each of the plurality of first portions includes:

an apex having the greatest curvature in the process of changing shape from the inflated state to the deflated state, a first extending portion extending to the apex from a connecting portion with at least one of the plurality of second portions adjacent to one side of the respective one of the plurality of first portions in the circumferential direction, and a second extending portion extending to the apex from a connecting portion with at least one of the plurality of second portions adjacent to an other side of the respective one of the plurality of first portions in the circumferential direction, and a length of the second extending portion is longer than a length of the first extending portion.

16. The balloon for a catheter according to claim 1, wherein each of the plurality of first portions includes an apex having the greatest curvature in the process of changing shape from the inflated state to the deflated state, and in the process of changing shape from the inflated state to the deflated state, a distance between the apex and at least one of the plurality of second portions adjacent to an other side of a respective one of the plurality of first portions in the circumferential direction with respect to the apex of the respective one of the plurality of first portions is longer than a distance between the apex and at least another one of the plurality of second portions adjacent to one side of the respective one of the plurality of first portions in the circumferential direction.

17. The balloon for a catheter according to claim 1, wherein each of the plurality of first portions includes an apex having the greatest curvature in the process of changing shape from the inflated state to the deflated state, a first extending portion extending to the apex from a connecting portion with at least one of the plurality of second portions adjacent to one side of the respective one of the plurality of first portions in the circumferential direction, and a second extending portion extending to the apex from a connecting portion with at least one of the plurality of second portions adjacent to an other side of the respective one of the plurality of first portions in the circumferential direction, and in the process of changing shape from the inflated state to the deflated state, at least a portion of the first extending portion of at least one of the plurality of first portions including the apex is disposed on the other side of the at least one of the plurality of first portions in the circumferential direction with respect to a virtual plane extending in the radial direction and passing through the center axis and the apex.

18. The balloon for a catheter according to claim 1, wherein, in the inflated state:

each of the plurality of first portions and the plurality of second portions include an inner surface facing an interior of the balloon; and each of the inner surfaces is separated from each of the other inner surfaces in the radial direction.

* * * * *